United States Patent [19]
Aita et al.

[11] Patent Number: 5,380,316
[45] Date of Patent: Jan. 10, 1995

[54] METHOD FOR INTRA-OPERATIVE MYOCARDIAL DEVICE REVASCULARIZATION

[75] Inventors: Michael Aita, Sunnyvale, Calif.; Mahmood Mirhoseini; Mary Cayton, both of Glendale, Wis.; Carl J. Simpson; Brian Guscott, both of Los Altos Hills, Calif.

[73] Assignee: Advanced Cardiovascular Systems, Inc., Sunnyvale, Calif.

[21] Appl. No.: 79,699

[22] Filed: Jun. 16, 1993

Related U.S. Application Data

[63] Continuation of Ser. No. 630,259, Dec. 18, 1990, abandoned.

[51] Int. Cl.⁶ ............................................. A61B 17/36
[52] U.S. Cl. ........................................ 606/7; 606/15; 606/16
[58] Field of Search ...................... 606/2, 3, 7, 13, 14, 606/15, 16, 17; 128/397, 398

[56] References Cited

U.S. PATENT DOCUMENTS 4,860,743  8/1989  Abela ................................. 606/16 X
4,890,898  1/1990  Bentley et al. ................... 606/16 X
4,967,745  11/1990 Hayes et al. ...................... 606/15 X

OTHER PUBLICATIONS

Jeevanandam, et al., "Myocardial Revascularization by Laser-Induced Channels", Surgical Forum XLI, 225-227 (Oct. 1990).
Hardy, et al., "Regional Myocardial Blood Flow and Cardiac Mechanics in Dog Hearts with $CO_2$ Laser-Induced Iniramyocardia Revascularization", basic Res. Cardiol. 85:179-197 (1990).
Mirhoseini, et al., "Clinical and Histological Evaulation of Laser Myocardial Revascularization", Journal of Clinical laser Medicine & Surgery, 73-78 (Jun. 1990).
Mirhoseini, et al. "Laser in Cardiothoracic Surgery", in Lasers in General Surgery (Joffe, Editor), Williams and Wilkins, 216-232 (1989).
Mirhoseini, et al. "New Concepts in Revascularization of the Myocardium", A Thorac. Surg. 45:415-420 (Apr. 1988).
Mirhoseini, et al., Clinical Report: "Laser Myocardial Revascularization", Lasers in Surgery and Medicine 6:49-461 (1986).
Mirhoseini, et al., "Myocardial Revascularization by Laser: A Clinical Report", Lasers in Surgery and Medicine 3:241-245 (1983).
Mirhoseini, et al., "Revascularization of the Heart by Laser", Journal of Microsurgery 253-260 (Jun. 1981).
Mirhoseini, "Laser Applications in Thoracic and Cardiovascular Surgery", Medical Instrumentation, vol. 17, No. 6, 401-403 (Nov.-Dec. 1982).
Mirhoseini, "Laser Revascularization of the Heart", in New Frontiers in Laser Medicine and Surgery (Atsumi, Editor), ISBN Elsevier Science Publishing Co., 296-303 (1982).
Mirhoseini, et al., "Transverniricular Revascularization by Laser", Lasers in Surgery and Medicine 2:187-198 (1982).

Primary Examiner—Peter A. Aschenbrenner
Attorney, Agent, or Firm—Crosby, Heafey, Roach & May

[57] ABSTRACT

The method for intra-operative myocardial revascularization of a human heart includes a inserting a portion of an elongated flexible lasing apparatus into the chest cavity of a patient, and lasing channels from the epicardium through the myocardium of the heart, without mechanical tearing of the heart tissue. The apparatus is guided to an area exterior to a ventricle of the patient's heart, and the distal end of the optical fiber apparatus is directed to an area of interest where the exterior wall of the heart is irradiated with laser energy to form a channel through the myocardium.

15 Claims, 1 Drawing Sheet

METHOD FOR INTRA-OPERATIVE MYOCARDIAL DEVICE REVASCULARIZATION

This is a continuation of copending application Ser. No. 07/630,259 which was filed on Dec. 18, 1990 now abandoned.

FIELD OF THE INVENTION

This invention is generally directed to the field of laser surgery, and more particularly to laser surgery procedures to improve the flow of blood to the heart muscle.

BACKGROUND OF THE INVENTION

The number and variety of medical methods available to repair the effects of cardiovascular disease has increased rapidly over the last several years. More particularly, alternatives to open heart surgery and cardiovascular by-pass surgery have been extensively investigated, resulting in non-surgical procedures such as percutaneous transluminal coronary angioplasty, laser angioplasty, and atherectomy. These procedures are primarily directed toward the reduction of stenosis within the vasculature of a patient by either expanding the lumen through the use of a balloon, or ablating or otherwise removing the material making up the stenosis.

While these procedures have shown considerable promise, many patients still require bypass surgery due to such conditions as the presence of extremely diffuse stenotic lesions, the presence of total occlusions and the presence of stenotic lesions in extremely tortuous vessels. Also, some patients are too sick to successfully undergo bypass surgery, and because the above treatments require surgical backup in the case of complications, they are untreatable. Some patients requiring repeat bypass surgeries are also untreatable.

One alternative to these procedures is known as Laser Myocardial Revascularization (LMR). In LMR, channels are formed in the ventricle wall with a laser. These channels provide blood flow to ischemic heart muscle. A history and description of this method is presented by Dr. M. Mirhoseini and M. Cayton in "Lasers in Cardiothoracic Surgery" in *Lasers in General Surgery* (Williams & Wilkins; 1989) pp. 216–223.

In the procedure described therein, a $CO_2$ laser is used to produce channels in the ventricle from the epicardium through to the myocardium. This procedure follows a surgical cutdown. External pressure is used to stop bleeding from the ventricle to the outside. Dr. Mirhoseini has documented that although the channel is sealed at the epicardial layer, it remains patent in the endocardial and myocardial layers. Laser energy is transmitted from the laser to the epicardium by means of an articulated arm device that is commonly used for $CO_2$ laser surgery.

A proposed improvement in the design is described in Hardy—U.S. Pat. No. 4,658,817. A needle is added to the distal tip of the articulated arm system, with laser energy passing through the lumen of the needle. The metal tip of the needle of the device is used to pierce most of the myocardium and the laser beam is used to create the desired channel through the remaining portion of the myocardium and through the adjacent endocardium.

Hardy contends that mechanical piercing serves to facilitate sealing of the epicardial portion of the channel. Mechanical piercing is highly undesirable, because such piercing always entails some degree of tearing of the pierced tissue. Tearing leads to fibrosis as the mechanical tear heals. Fibrosis severely diminishes the effectiveness of the LMR treatment.

These LMR procedures still require that the chest wall be opened in order to access the heart muscle with presently utilized laser devices. Thus these procedures require major surgery which is highly invasive and which may result in severe complications.

An additional problem associated with those procedures utilizing an articulated arm device is that the articulated arm is difficult to manipulate. Thus portions of the heart may be effectively unreachable by the device.

Broadly, it is the object of the present invention to provide an improved method for performing laser myocardial revascularization.

It is a further object of the present invention to provide a less invasive method for performing laser myocardial revascularization.

It is a still further object of the present invention to provide a method for performing laser myocardial revascularization which can access difficult to reach portions of the heart.

It is a yet further object of the present invention to provide a method for performing laser myocardial revascularization which does not require mechanical perforation of heart tissue.

These and other objects of the present invention will be apparent to those skilled in the art from the following detailed description and the accompanying drawings.

SUMMARY OF THE INVENTION

The present invention comprises a method of intra-operative myocardial revascularization of the myocardium of the heart of a patient. An elongated flexible lasing apparatus is inserted into the chest cavity of the patient. The distal end of the lasing apparatus is then guided to an area immediately adjacent and exterior to the patient's heart. The exterior wall of the heart is next irradiated with laser energy emitted from the distal end of the lasing apparatus with sufficient energy and for a sufficient time to cause a channel to be formed from the exterior surface of the epicardium through the myocardium and the endocardium. An exterior portion of the channel is then sealed.

DETAILED DESCRIPTION OF THE PREFERRED EMBODIMENT

Figure 1:
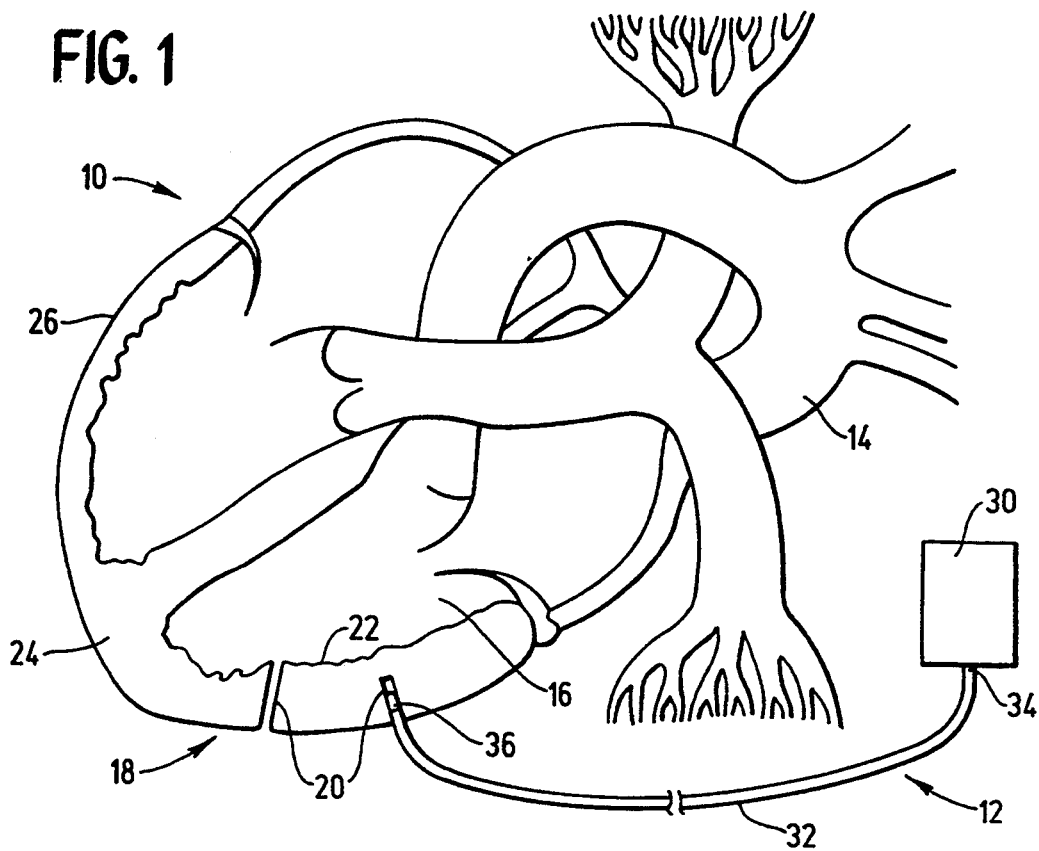
FIG. 1 is a schematic section of a human heart showing revascularization of the myocardium according to the invention.

As is shown in the drawings, which are provided for purposes of illustration and not by way of limitation, an apparatus suitable for implementing the present invention is embodied in a system for revascularization of the myocardium of a human heart 10. As is illustrated in FIG. 1, the elongated flexible lasing apparatus 12 is placed adjacent to an area such as a ventricle 16 having an area 18 in need of increased blood circulation due to cardiovascular disease. Lasing apparatus 12 may include either an optical fiber adapted to a laser or a waveguide adapted to a $CO_2$ laser or other laser. Portions of the heart other than ventricles might also be revascularized by this method. A number of channels 20 can be formed by the shapeable elongated flexible lasing apparatus from the outer wall, or epicardium 26, and extend a through the myocardium 24 and perforating the interior of the heart wall, the endocardium 22.

The elongated flexible lasing apparatus 12 includes a remotely located source of laser energy 30 connected to the proximal end 34 of an optical fiber 32. Laser 30 may typically be a $CO_2$ laser, or an HO YAG laser, for example, although other sources of energy, such as excimer lasers, are adaptable to the invention. $CO_2$ lasers would require an appropriate optical waveguide 32. Optical fiber 32 conducts the laser energy to its distal end 36.

Figure 2:
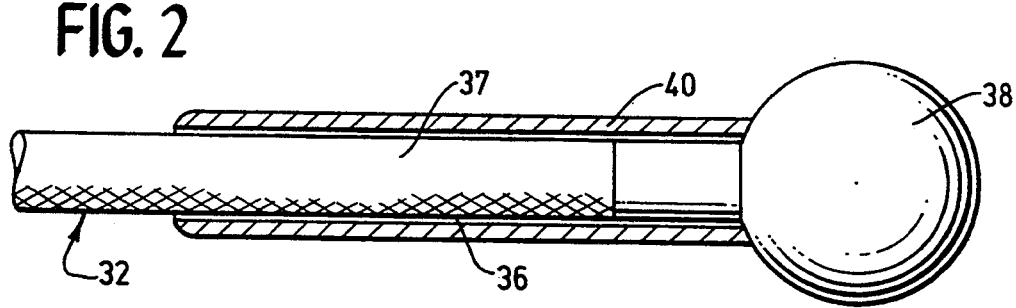
FIG. 2 is a schematic cross-section of an elongated flexible lasing apparatus suitable for the method of the invention.
Figure 3:
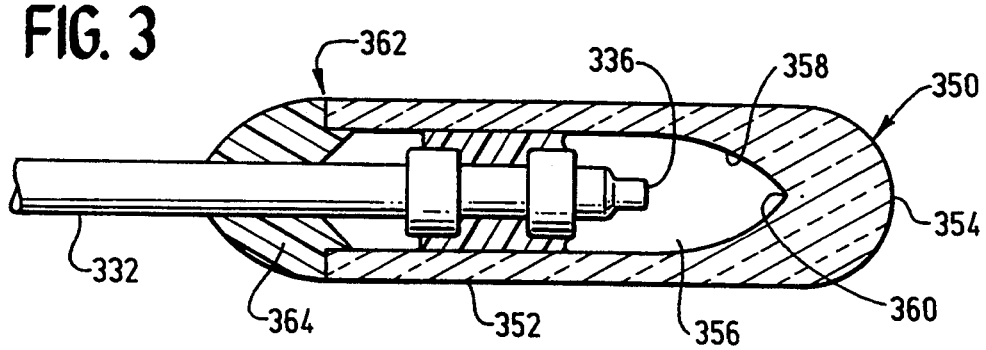
FIG. 3 is a cross-section of a preferred lens design for the invention.

Referring to FIG. 2, a lens 38 having a sleeve 40, is preferably connected to the distal end 36 of optical fiber 32. Although lens 38 is illustrated in FIG. 2 as being a ball type lens, the preferred embodiment of lens 38 is illustrated in FIG. 3, which is discussed below. Lens 38 controls the output spatial distribution of the laser energy emitted by optical fiber 32.

In a preferred embodiment of an apparatus adapted for the present method, a portion of distal end 36 of optical fiber 32 is adapted to be shaped into a desired configuration. Such a shapeable fiber apparatus is disclosed in co-pending application U.S. Ser. No. 605,774 by Samson, assigned to Advanced Cardiovascular Systems. A tubular metallic braid 37 is placed over and affixed to a section of distal end 36 of optical fiber 32. This allows optical fiber 32 to retain its shape in a desired configuration.

Referring to FIG. 3, it has been found that in a preferred embodiment of the invention, a lens 350 is configured to include an essentially cylindrical outer surface 352 terminating in a convex distal tip 354. An optical fiber 332 extends into an internal cavity 356 and terminates in a position spaced apart from an internal aspheric or ogival shaped surface 358, the cavity apex 360 of which is distal from distal end 336 of fiber 332. The interface 362 between optical fiber 332 and lens 350 is reinforced, preferably with epoxy 364 or the like, although other means of reinforcement designed to prevent dislodging of the lens are adaptable to the invention.

The basic method of the present invention has been laid out above. The shapeable elongated flexible lasing apparatus 12 is inserted into the chest cavity. This insertion may require only a small incision, which would minimize the invasiveness of the procedure. Lasing apparatus 12 is then placed adjacent an area such as a ventricle 16 having an area 18 in need of increased blood circulation due to cardiovascular disease. This placement may be facilitated by shaping the fiber into a desired configuration. A number of channels 20 can then be formed by the shapeable elongated flexible lasing apparatus 12 from the outer wall, or epicardium 26, and extend through the myocardium 24 and perforating the interior of the heart wall, the endocardium 22.

In operation, the distal end of the optical fiber apparatus may be maintained in position on the outer heart wall by a gentle pressure, to insure that the apparatus is not dislodged in the formation of the channel between pulses of the laser. The heart beat is preferably monitored, and the laser is preferably gated to generate one or more pulses during contractions (systole) of the heart, and to generate no pulses during the rest of the heart cycle. These procedures combine to anchor the apparatus to a relatively stable location on the tissue that is to be ablated.

In early experiments with a HO laser, it was found that it may be desirable to begin the procedure with approximately 0.65 j pulses, at a frequency of at least 2 Hz, in order to penetrate the endocardium, and then decrease the laser power to approximately 0.2 j to form the channel in the myocardium. This minimizes the need for anchoring the catheter to the area to be treated. Note that the dosimetry is dependent upon the diameter of the lens used.

In practice, it has been found that the lens of the embodiment of FIG. 3, when in contact with tissue, cuts a lumen equal or greater than the lens diameter which is in front of and axially aligned with the axis of the lens. This provides improved ablation of channels into the heart muscle of the type preferred in this method. As the channel is cut, the cylindrical outer surface 352 assists in guiding and controlling the catheter during the cutting process. The angle of the projected energy from the lens can also be controlled by some degree with the separation of distal tip 336 of optical fiber 332 from the cavity distal apex 360. It has also been found that the construction is scalable.

It has been found that channels that are approximately 1.5 mm–2.0 mm in diameter and approximately 1 to 3 cm deep may easily and efficiently be cut by this method, and that the revascularization procedure dramatically improves the flow of blood to the heart muscle, thereby decreasing the probability of heart attack from occlusion of the external vasculature of the heart.

Once the channel is formed the portion of the channel opening through the epicardium is temporarily covered while a portion of the channel extending through the epicardium seal itself.

There has been described herein a method of performing laser revascularization of the heart. Various modifications to the present invention will become apparent to those skilled in the art from the foregoing description and accompanying drawings. Accordingly, the present invention is to be limited solely by the scope of the following claims.

What is claimed is:

1. A method of revascularizing a desired portion of a patient's myocardium, comprising the steps of:
   providing an elongated flexible optical fiber system having proximal and distal ends;
   guiding a distal portion of the elongate flexible optical fiber system within the patient's chest cavity and urging the distal end thereof into contact with an exterior portion of the patient's epicardium which is extensive with the desired portion of the myocardium to be revascularized; and
   transmitting laser energy from a remote source thereof through the optical fiber system to the distal end of said optical fiber system and directing transmitted laser energy emitted from the distal end thereof in a beam onto the portion of the patient's epicardium in contact therewith with sufficient energy and for a sufficient length of time to form a revascularizing channel through the epicardium, the myocardium and the endocardium having transverse dimensions at least the same as the distal end of the optical fiber system while urging the distal end of the optical fiber system against tissue thereof.

2. The method of claim 1 further including the steps of monitoring the systole and diastole of the patient's heart, and performing said step of directing laser energy onto the epicardium of the patient's heart with transmitted laser energy in a plurality of pulses during systole of the heart.

3. The method of claim 1, wherein a portion of said elongated flexible lasing apparatus is capable of being shaped and supported in a desired configuration, and wherein said guiding of said elongated flexible lasing apparatus further comprises shaping said portion into a desired configuration.

4. A method of increasing the flow of blood within a patient's heart by forming at least one channel through an exterior wall of the patient's heart into a heart chamber defined by the wall, comprising the steps of:
   directing a distal portion of an elongated flexible lasing system having a distal end into the patient's chest cavity;
   guiding the distal end of the flexible lasing system within the patient's chest cavity to engage an exterior area of the wall of the patient's heart in which increased blood flow is desired; and
   directing laser energy in a beam from the distal end of said flexible lasing system in a plurality of pulses during individual heart beats to create a revascularizing channel in the wall of the patient's heart and guiding the distal end of the flexible lasing system in the channel created while creating the channel until the channel extends into and is in communication with heart chamber defined by the wall.

5. The method of claim 4, wherein a lens having a diameter of not greater than about 2 mm is provided on the distal end of the flexible lasing system and wherein laser energy transmitted through the flexible lasing system is focused into a beam to form the channel.

6. The method of claim 4, further including the steps of monitoring the systcle and diastole of the heart, and performing said step of directing said laser energy emission on the exterior wall of the heart in a plurality of pulses during systole of the heart.

7. The method of claim 5 wherein a portion of said elongated flexible lasing system is capable of being shaped and supported in a desired configuration, and wherein the guiding of said elongated flexible lasing apparatus further comprises shaping said portion into a desired configuration.

8. The method of claim 1 wherein a lens having a diameter of not greater than about 2 mm is provided on the distal end of the optical fiber system and wherein laser energy transmitted through the optical fiber system is directed through the lens onto the epicardium layer of the patient's heart to form a revascularizing channel therein having a diameter of about 1.5 to about 2 mm.

9. The method of claim 5 wherein a lens having a diameter of not greater than about 2 mm is provided on the distal end of the optical fiber system and wherein laser energy transmitted through the optical fiber system is directed through lens onto the wall of the patient's heart to form a revascularization channel therein having a diameter of about 1.5 to about 2 mm.

10. The method of claim 1 wherein the laser energy is transmitted through the optical fiber in a plurality of pulses during the patient's systole.

11. The method of claim 1 wherein the laser energy is at a first energy level when passing thorugh the patient's epicardium and at a second energy level lower than the first when passing through the patient's myocardium.

12. The method of claim 1 wherein the distal portion of the optical fiber system is passed into the patient's chest cavity through a small incision in the patient's chest.

13. The method of claim 1 wherein a lens having a diameter of not greater than about 2 mm is provided on the distal end of the optical fiber system and wherein laser energy transmitted through the optical fiber system is directed through the lens to facilitate advancement of the optical fiber through the revascularizing channel as it is formed.

14. The method of claim 13 wherein the revascularization channel has a diameter not more than about 0.5 mm greater than the lens.

15. The method of claim 5 wherein the revascularization channel has a diameter not more than about 0.5 mm greater than the lens mounted on the distal end of the flexible lasing system.

* * * * *

UNITED STATES PATENT AND TRADEMARK OFFICE
CERTIFICATE OF CORRECTION

PATENT NO. : 5,380,316

DATED : January 10, 1995

INVENTOR(S) : Mike Aita et al.

It is certified that error appears in the above-identified patent and that said Letters Patent is hereby corrected as shown below:

```
Column 5:
Claim 6, line 2, change "systcle" to --systole--.
```

Signed and Sealed this

Eighteenth Day of April, 1995

*Attest:*

BRUCE LEHMAN

*Attesting Officer*

*Commissioner of Patents and Trademarks*